United States Patent
Lanzi

(10) Patent No.: US 11,311,468 B2
(45) Date of Patent: Apr. 26, 2022

(54) HAIR COLORING COMPOSITION AND RELATED COLORING KIT

(71) Applicant: Unicompany S.P.A., Ardea (IT)

(72) Inventor: Gabriele Lanzi, Pieve Santo Stefano (IT)

(73) Assignee: Unicompany S.P.A., Ardea (IT)

(*) Notice: Subject to any disclaimer, the term of this patent is extended or adjusted under 35 U.S.C. 154(b) by 0 days.

(21) Appl. No.: 17/026,232

(22) Filed: Sep. 20, 2020

(65) Prior Publication Data

US 2021/0128426 A1 May 6, 2021

(30) Foreign Application Priority Data

Sep. 20, 2019 (IT) .................. 102019000016904

(51) Int. Cl.
| | | |
|---|---|---|
| *A61Q 5/10* | (2006.01) | |
| *A61K 8/22* | (2006.01) | |
| *A61K 8/04* | (2006.01) | |
| *A61Q 5/06* | (2006.01) | |

(52) U.S. Cl.
CPC .................. *A61K 8/22* (2013.01); *A61K 8/04* (2013.01); *A61K 2800/4324* (2013.01); *A61Q 5/065* (2013.01); *A61Q 5/10* (2013.01)

(58) Field of Classification Search
CPC . A61Q 5/10; A61K 8/22; A61K 8/411; A61K 8/4926; A61K 8/415; A61K 2800/4324; A61K 8/41; A61K 2800/882; A61K 8/347; A61K 8/042; A61K 8/04
USPC .............................................. 8/405
See application file for complete search history.

(56) References Cited

U.S. PATENT DOCUMENTS

| | | |
|---|---|---|
| 2002/0179109 A1 | 12/2002 | Lenzi-Brangi et al. |
| 2010/0192969 A1* | 8/2010 | DeGeorge ............... A61K 8/23 |
| | | 132/208 |
| 2010/0313362 A1 | 12/2010 | Vainshelboim et al. |
| 2011/0247644 A1 | 10/2011 | Oberkobusch et al. |
| 2012/0048288 A1 | 3/2012 | Reichert et al. |
| 2019/0117549 A1 | 4/2019 | Degeorge et al. |

OTHER PUBLICATIONS

Rapporto di Ricerca e Opinione Scritta [Search report and Written Opinion] dated Jun. 11, 2020 From the Ministerio Dello Sviluppo Economico, Direzione Generale Sviluppo Produttivo e Competitivita, Ufficio Italiano Brevetti e Marchi Re. Application No. IT 201900016904. (11 Pages).

* cited by examiner

*Primary Examiner* — Eisa B Elhilo

(57) ABSTRACT

The present invention relates to a hair coloring composition based on natural ingredients and with a separate alkalizing agent, which can be used both in direct coloring and oxidative coloring and related coloring kit.

14 Claims, No Drawings

HAIR COLORING COMPOSITION AND RELATED COLORING KIT

RELATED APPLICATION

This application claims the benefit of priority of Italian Patent Application No. 102019000016904 filed on Sep. 20, 2019, the contents of which are incorporated herein by reference in their entirety.

FIELD AND BACKGROUND OF THE INVENTION

The present invention relates to a hair coloring composition and a related coloring kit.

In greater detail, the invention relates to a hair coloring composition based on natural ingredients and without an alkalizing agent which can be used both in direct coloring and oxidative coloring and a related coloring kit.

As is well known (see also "The Science of Hair Care" by Charles Zviak), various types of coloring exist, but from a chemical viewpoint they can be distinguished into two large branches: direct and oxidative. The products for direct coloring contain dyes (only direct and non-oxidative) and alkalizing agents (if necessary, but they are not always present because their pH can also be acidic or neutral), but they do not provide for mixing with a third component that contains hydrogen peroxide. These products, as the term itself says, can be applied "directly" on the fiber to be colored. Direct coloring products are already capable of absorbing or emitting luminous radiation in the visible spectrum due to their chemical nature, i.e. due to the presence of functional groups (AUXOCHROMES and CHROMOPHORES), without having to undergo further modifications. They are thus already ready and capable of coloring hair directly, without any oxidation and simultaneous decolorization mechanisms being involved. However, the color obtained with direct coloring is shorter lasting.

Oxidative coloring products use different molecules from the ones used in direct coloring products. More specifically, oxidative products use oxidation intermediates, which do not color by themselves (because they do not contain auxochrome and chromophore groups), but which, once they have come into contact with a source of oxygen (the most commonly used is hydrogen peroxide, precisely), undergo a chemical reaction that leads them to become larger molecules endowed with the above-mentioned functional groups, necessary to "color", i.e. to express the coloring. Oxidative coloring products represent the type of coloring that allows the natural color of the hair to be lightened or darkened, and the reflections thereof to be intensified or modified, guaranteeing a lasting and persistent result. Oxidative coloring products contain dyes and alkalizing agents in a predefined amount and, at the time of use, the oxidizing compound is added to them.

There are essentially three known types of oxidative coloring:

with an acidic pH, which uses insignificant or zero amount of alkalizing agent (the most commonly used as alkalizing agents are ammonia, in the form of ammonium hydroxide, or other types of amines, such as, for example monoethanolamine, tris (tris(hydroxymethyl)aminomethane), aminomethyl propanol). The products for this type of coloring are called glosses and/or mild, ammonia-free colorings, also named GLOSS (glossing agents) which in general refer to products in the market, such as REDKEN SHADES EQ™ and others;

with a medium basic pH, which uses larger amounts of alkalizing agent compared to gloss colorings, and with which one obtains a series of tone-on-tone and DEMI-PERMANENT colorings, which in general refer to products in the market, such as COLOR TOUCH WELLA™ or others like THE DEMI from PAUL MITCHELL™;

with basic pH, which uses even larger amounts of an alkalizing agent, and with which one obtains a series of permanent colorings, which are in general the most common (L'OREAL MAJIREL™, KOLESTON PERFECT WELLA™ and many others).

Ammonia is the most widely used alkalizing agent in permanent colorings, whereas in gloss and demi colorings, the most widely used alkalizing agents are monoethanolamine and aminomethyl propanol (the latter two, not being gases, do not emit unpleasant odors).

Coloring products can be formulated in a cream, oil or gel base containing the dyes or the oxidation intermediates thereof, and one or more alkalizing agents. As mentioned above, the latter can be ammonia, normally included as ammonium hydroxide (in some rare cases also in other forms), monoethanolamine, for the so-called "ammonia-free" colorings, aminomethyl propanol and some derivatives thereof, effective only in demi-permanent colorings with a medium basic pH.

As mentioned above, in an oxidative coloring, at the time of use of the dye, an oxidizing agent such as, for example, hydrogen peroxide (contained in well-defined volumes, in aqueous solutions or more or less viscous emulsions) is added.

In all the dyes present in the market, the alkalizing agent is already present within the cream, oil or gel base in different percentages depending on the type of final service it is desired to obtain (i.e. GLOSS, DEMI-PERMANENT or PERMANENT colorings). In the known dyes, the alkalizing agent is in a free form, in addition to the percentage of alkalizing agent bound to the dyes contained in the formulation.

In other words, there are commercially available coloring products for acidic pH coloring, containing insignificant or zero amounts of alkalizing agent, for medium basic pH coloring, containing larger amounts of alkalizing agent, and for basic pH coloring, with even larger amounts of alkalizing agent.

Though on the one hand these products with a predefined content of an alkalizing agent assure reproducibility in the coloring result, on the other hand they oblige the professional to use several products in order to apply different coloring methods. For example, a professional could wish to apply different GLOSS, DEMI-PERMANENT or PERMANENT coloring methods on different lengths or portions of a person's hair. In this case, the professional would have to use several products with corresponding costs and waste of material. Furthermore, since very few companies supply all lines of GLOSS, DEMI-PERMANENT or PERMANENT colorings, a professional who purchases the various lines of colorings from different manufacturers could encounter phenomena of incompatibility or inconsistency with the type of service. More specifically, when choosing the gloss to be applied, every manufacturer delivers a different result, and this obliges the hairstylist to know exactly the result of each individual product in order to have a result that is homogeneous from the root to the ends. Furthermore, the trend today is to move ever nearer to the natural world, and therefore to products that respect man and the environment. For example, if a professional intended to achieve a "green" color, i.e. formulated with natural ingredients, and wanted to do so with the products made available by the market, he/she would not be able to assure the linearity of philosophy and concept that the customer expects, because he/she would have to use a natural product for the lengths, but would not have at his/her disposal a natural product for the roots. Therefore, the professional would do only half the job with a "natural" product, or would have to rely on a natural line suitable for coloring the roots (permanent coloring with an alkaline pH) and then use another natural line to color the lengths (coloring with an acidic or medium basic pH). This choice would oblige the hairstylist to purchase various lines of colorings and be exactly acquainted with all of the tones proposed, so as to create a perfect harmony and combination between the color at the roots and the one on the lengths. Very often, in the cases, it may happen that the hairstylist, out of fear of making a mistake or to avoid investing money in so many color lines, which would be difficult to maintain in a salon, carries out a coloring treatment with a single product, from the roots to the ends, losing the personalization of the treatment and also ending up performing wrong treatments on hair fibers. In fact, where there is no need for alkalinity, for example, in the case of the lengths, it would be preferable and advisable to use a mild product, with an acidic or medium basic pH for the lengths, which are generally more brittle, older or perhaps more treated, because subjected to various coloring and/or decolorizing processes. Even when the professional relies on the use of different products and different coloring lines, he/she would have at his/her disposal defined concentrations for each type of coloring without the possibility of making personalized adjustments to the content of alkalizing agent.

There are some known coloring products, whereby it has been attempted to overcome the above-mentioned disadvantages, containing a high percentage of alkalizing agent and which, at the time of use, are added with products capable of reducing the alkalinity based on the type of coloring to be applied among colorings of an acidic, medium basic and basic type. However, these products have revealed to be suitable only for coloring of a basic type, since the obtainable reduction in alkalinity has not proven to be sufficient to enable other types of coloring. Furthermore, this type of product leads to a greater use and waste of alkalizing agent, in addition to the use of further chemical compounds such as the alkalinity reducing agent. Finally, the use of these phantasmic "alkalinity reducers" does not solve the problem of milder, more delicate and personalized treatments on the lengths.

In addition to what has been described above, it is noted that the hair coloring products generally contain toxic or pollutant substances or substances which are sometimes simply not admitted or ill-regarded in some countries, such as, for example, COCAMIDE MEA and DEA, ETHYL ALCOHOL, ISOPROPYL ALCOHOL, DERIVATIVES OF PETROLEUM or PARAFFINS, PARABENS, SLS, SLES, INGREDIENTS OF ANIMAL ORIGIN, SILICONES, and products obtained by ethoxylation.

In the light of the above, there appears to be an evident need to be able to have new hair coloring products capable of overcoming the disadvantages of the known products.

SUMMARY OF THE INVENTION

Fitting into this context is the solution according to the present invention, which aims to provide a formulation with the highest possible content of natural ingredients, suitable for both direct coloring and oxidative coloring, and which is versatile in professional use without any waste of product.

These and other results are obtained according to the present invention by proposing a coloring composition containing from 85% to 98% of natural ingredients, and containing no alkalizing agents in a free form (during the preparation of the coloring composition, use is made of a small amount of alkalizing agent which, in the final formulation, is present in a form bound to the dyes). The base formulation according to the invention boasts a wholly natural CHASSIS, based on natural ingredients and ingredients of natural origin. Classic hair dyes are added to this CHASSIS (specifically, OXIDATION INTERMEDIATES and DIRECT DYES) which are synthetic rather than natural, but which represent the lowest percentage within the formulation.

In addition to providing a formulation comprising a high content of natural ingredients, the present invention enables various services to be obtained with a single product, i.e. the formulation of the invention can be used in various ways, such as with an acidic pH, a medium basic pH and a basic pH. This means that with a single line of dyes one can cover a vast range of hair coloring products and different treatments (or services).

The present invention envisages that the alkalizing agent (such as, for example, AMMONIA) can be added at the time of use in different amounts (according to a well-defined scheme), depending on the type of coloring desired among GLOSS, DEMI-PERMANENT and PERMANENT and on the type of coloring with dark, brown and blond colors. AMMONIA would be preferred among the alkalizing agents, given both its natural derivation and the fact that, according to by now well-known studies, it is the least aggressive alkalizing agent for skin and hair. Because of its volatility, one can perceive its classic unpleasant odor during application; at the same time, however, its volatility prevents the hair scales from opening excessively, ensuring that the pH level and the opening of the hair cuticles become normalized during the setting time (time during which all the ammonia present has evaporated).

Summing up, the world of oxidative hair coloring envisages three different types of treatment:
1) GLOSS, with an acidic pH
2) DEMI-PERMANENT, with a medium basic pH
3) PERMANENT, with an alkaline pH To date the market has offered various types of products for the various coloring categories.

The present invention, by contrast, offers only one type of product which can be personalized at the time of the treatment and application.

The advantages provided by the invention are for example:

a complete personalization of the treatment based on the needs of the customer, whether of a young age and therefore at the first coloring experiences and without any white hair, or of a middle age with other needs, or of an advanced age with yet other needs and a different hair structure;

personalization of the treatment depending on the different situation that a professional has to confront with a single customer (for example hair that needs the roots to be colored in a certain way, perhaps due to the presence of white hair in various percentages, and the lengths and ends in a different way, due, for example, to the presence of highlights, lightening, balayage, shatush, degrade or other effects);

guarantee of a uniform result, since the professional is using a single coloring line that he/she personalizes in a simple manner.

Added to these advantages is the one of not having to study and learn the use of a large number of different colorings belonging to the various lines of products that the market offers, as it will be sufficient to learn to use only the product of the invention.

By using a single product such as the one according to the present invention, professionals will have the possibility of personalizing the treatment, enabling them to distinguish themselves and to achieve a high quality, uniform result with a method that is simple to apply.

Furthermore, the coloring product according to the present invention is a product defined as GREEN, or natural, both in the acidic pH form thereof and in the extreme alkaline pH form thereof. Therefore, the product of the invention makes it possible to obtain high performance, a uniform coloring and thus an elegant result by means of a natural product that respects man and the environment.

Going into the specifics of the formulation, the base coloring composition of the present invention can comprise:
one or more natural solvents in a percentage ranging from 0.1% to 90%, preferably from 1% to 20%, by weight with respect to the base coloring composition itself;
one or more natural surfactants in a percentage ranging from 0.1% to 30%, preferably from 0.5% to 5%, by weight with respect to the total base composition;
viscosifiers (or natural rheology modifiers) in a percentage ranging from 0.01% to 10%, preferably from 0.05% all 1.5%, by weight with respect to the total base composition or consistency factors in a percentage ranging from 1% to 50%, preferably from 10% to 30% by weight with respect to the total base composition; and
dyes or their oxidation intermediates in a percentage that can vary according to the shade (or nuance) and the combination selected by the formulator. The dye can be present in variable amounts. For example, the dyes or their oxidation intermediates can be present in an amount ranging from about 0.3% in a light shade to about 6% in a dark shade, said percentages being by weight with respect to the total base coloring composition.

The natural solvents can be PROPANEDIOL, or waters and hydrolates, essential waters, vegetable glycerine, various oils, vinegar, sugar and many others.

According to the present invention, the surfactants can be selected from all those of natural origin, obtained for example from oil or coconut palms, wheat, sugar or other fat-rich plants and which in any case have not been subjected to an ethoxylation process.

The viscosifiers for the preparation of a gel formulation according to the present invention can for example be selected from XANTHAN GUM, similar natural gums, such as, for example, *SCLEROTIUM* GUM, GUAR GUM, GUM ARABIC and all others derived from sugars and components of natural origin.

The consistency factors for the preparation of a cream formulation according to the present invention can for example be selected from waxes, alcohols of fatty acids and/or fatty acids. Furthermore, the composition can contain emulsifiers, such as oils, and conditioning agents. For example, the composition can contain oils and/or waxes that serve to create the texture of the product, for example for the preparation of creams, which can be selected from all those allowed under one of the best known standards, e.g. COSMOS, NATRUE, CCPB, AIAB, ICEA, DEMETER, ECOCERT and others (see revisions of September 2019).

The base composition without the dyes can also be used to prepare an alkalizing composition and an oxidizing composition to be used in combination with the coloring composition itself, as described below and in the examples.

The dyes or oxidation intermediates are selected from all those allowed under European regulations (REGULATION (EC) No 1223/2009 OF THE EUROPEAN PARLIAMENT AND OF COUNCIL of 30 Nov. 2009 on cosmetic products and annexes thereto) and in the allowed percentages (SCCS Scientific Committee on Consumer Safety and SCCP Scientific Committee on Consumer Products). The list of dyes is vast, but known to formulators of hair dyes.

As said above, at the time of use the coloring formulation (or base formulation) of the invention is added with an alkalizing agent.

The alkalizing agent can be selected from amines of various types (monoethanolamine, aminomethyl propanol, tris, etc.), preferably ammonia.

The alkalizing composition comprises a percentage that varies according to the type of agent selected and the specific shade, again in observance of the limits set by regulations (REGULATION (EC) No 1223/2009).

In the formulation according to the present invention, the alkalizing agent is added to the coloring formulation at the time of use in the percentages shown below based on the type of coloring desired and the color or shade that has been selected for the specific application. Table 1 shows the percentages of alkalizing agent (expressed as absolute AMMONIA and by weight with respect to the sum of the weight of the base coloring formulation and weight of the added booster) to be added under the conditions shown:

TABLE 1

| | Acidic pH coloring | Medium basic pH coloring | Basic pH coloring |
| --- | --- | --- | --- |
| For shades from 1 to 6 | 0% | From 0.5% to 1.2% (preferred value 0.8%) | From 1.2% to 2.8% (preferred value 1.6%) |
| For shades from 7 to 10 | 0% | From 0.7% to 1.8% (preferred value 1.0%) | From 1.8% to 3.5% (preferred value 2.0%) |
| Per super-lighteners (12.) | 0% | From 0.7% to 1.2% (preferred value 1.0%) | From 1.2% to 5% (preferred value 3.0%) |

The shade numbers are defined according to an international color classification system, recognized at the European level, which was defined by the French pharmacist EUGENE SCHUELLER as follows:
1. BLACK
2. DARKEST BROWN
3. DARK BROWN
4. BROWN
5. LIGHT BROWN
6. DARK BLONDE
7. BLONDE
8. LIGHT BLONDE
9. VERY LIGHT BLONDE
10. ULTRA LIGHT PLATINUM BLONDE The ammonia is added not in pure (volatile) form, but in liquid form (as ammonium hydroxide $NH_4OH$), being introduced into a finished cosmetic product which is also called a BOOSTER.

The liquid ammonia can for example have a pure ammonia concentration of 30%.

The BOOSTER according to the present invention contains distinct and defined percentages of liquid ammonia. In particular, according to the present invention, two types of BOOSTER are used based on the shades to be obtained, for example:

BOOSTER 01, which contains percentages of liquid ammonia equal to 27% and

BOOSTER 02, which contains percentages of liquid ammonia equal to 33%.

Summing Up:

| BOOSTER | % NH4OH | % absolute NH3 |
|---|---|---|
| BOOSTER 01 | 27% | 8.1% |
| BOOSTER 02 | 33% | 9.9% |

The percentages of liquid ammonia introduced into the BOOSTERS 01 and 02 are only non-limiting illustrative examples of the present invention. More specifically, it is possible to use different percentages both in the BOOSTER 01 and in the BOOSTER 02 so as to obtain the percentages of ammonia shown in table 1.

The BOOSTER is dosed by the hairstylist together with the coloring composition, according to specific procedures and amounts, defined and described in the product usage instructions, in order to obtain the absolute amount by weight of ammonia indicated in table 1.

Finally, in the case of an oxidative coloring, the oxidizing agent is added as well as the alkalizing agent, again at the time of use of the formulation of the invention. The oxidizing agent, both in the form of a liquid solution and in the form of an emulsion at various fat phase concentrations, must have a well-defined, declared volume, which can range from a minimum of 2.5 volumes (0.75%) to a maximum of 40 volumes (12%).

It is therefore a specific object of the present invention a hair cosmetic composition comprising:

one or more natural solvents in a percentage ranging from 0.1% to 90%, preferably from 1% to 20%;

one or more natural surfactants in a percentage ranging from 0.1% to 30%, preferably from 0.5% to 5% of surfactant;

one or more viscosifiers (or natural rheology modifiers) and/or consistency factors, optionally in combination with emulsifiers, wherein said viscosifiers are in a percentage ranging from 0.01% to 10%, preferably from 0.05% to 1.5%, whereas said consistency factors are in a percentage ranging from 1% to 50%, preferably from 10% to 30%;

said percentages being by weight with respect to the cosmetic composition, wherein said cosmetic composition further comprises direct dyes or their oxidation intermediates to obtain a coloring composition; or one or more alkalizing agents to obtain an alkalizing composition; or one or more oxidizing agents to obtain an oxidizing composition.

As mentioned above, the coloring composition according to the present invention does not contain alkalizing agents (such as, for example, ammonia) in a free form, that is, in a form not salified with the dyes, nor does it contain oxidizers or persulfates. Furthermore, the coloring composition according to the present invention does not contain dye-yielding plants.

Furthermore, the coloring composition according to the present invention comprises antioxidant compounds only in low percentages, such as, for example, percentages no higher than 0.4%, in order to stabilize the product and protecting it against oxidation, for example oxidation caused by contact with air. The coloring composition according to the present invention can be an oxidative coloring composition.

The composition according to the present invention, comprising the coloring composition, does not contain ethoxylated compounds, such as, for example, non-ionic emulsifier compounds with a different degree of ethoxylation; moreover, it is not a decolorizing composition.

The alkalizing composition according to the present invention comprises neither a dye nor an oxidizer.

The coloring composition according to the present invention can be either in the form of a gel or in the form of a cream. According to the present invention, viscosifiers are essential to obtain the gel compositions, whereas the consistency factors are essential to obtain the cream compositions. However, said viscosifiers can also be contained in the creams.

According to the present invention, the natural solvents can be selected in the group consisting of PROPANEDIOL, water, hydrolates, essential waters, vegetable glycerine, oils, vinegar, sugar.

According to one embodiment of the present invention, the viscosifiers can be gums selected from xanthan gum, similar natural gums such as, for example, *Sclerotium* gum, guar gum, gum arabic, gums derived from sugars and components of natural origin, whereas the consistency factors can be selected from waxes, alcohols of fatty acids and/or fatty acids.

The surfactants that can be used according to the present invention can be selected from surfactants of natural origin, obtained for example from oil or coconut palms, wheat, sugar or other fat-rich plants and which have not been subjected to an ethoxylation process.

According to one embodiment of the present invention, said cosmetic composition can be a coloring composition in the form of a gel and containing gums as viscosifiers.

The present invention further relates to a hair coloring kit comprising a) a coloring composition as defined above when the cosmetic composition comprises said dyes or their oxidation intermediates, and b) an alkalizing composition comprising one or more alkalizing agents, preferably as defined above, when the cosmetic composition comprises one or more alkalizing agents.

The alkalizing agents can be selected from amines of various types, such as, for example, ammonia, monoethanolamine, aminomethyl propanol or tris (tris(hydroxymethyl)aminomethane), preferably ammonia or formulations containing it.

According to one embodiment, the kit according to the present invention can further comprise c) an oxidizing composition comprising one or more oxidizing agents, such as hydrogen peroxide, preferably as defined above, optionally comprising acrylates, methacrylates or cellulose derivatives.

According to a particular embodiment of the present invention, the kit can comprise a) a coloring composition as defined above, in the form of a gel and containing gums as viscosifiers; b) an alkalizing composition comprising one or more alkalizing agents, such as ammonia or formulations containing it, preferably an alkalizing composition as defined above; and c) an oxidizing composition comprising one or more oxidizing agents, such as hydrogen peroxide, preferably an oxidizing composition as defined above, in the form of a cream or comprising ACRYLATES, METHACRYLATES or natural cellulose derivatives. This embodiment of the kit makes it possible to use very low percentages of viscosifier (for example about 1% or even less than 1% of xanthan gum) in the coloring composition and to obtain a viscosity that is appropriate for use when the oxidizing composition containing acrylates and methacrylates or other viscosifiers, for example in the form of an emulsion, is added to the coloring composition according to the present invention.

The present invention further relates to a hair coloring method comprising mixing a coloring composition a) of the kit as defined above with an alkalizing composition b) of the kit as defined above, wherein the composition b) is added to the composition a) in such an amount as to obtain from 0.5 to 10% of alkalizing agent.

According to the present invention, when the alkalizing composition is an ammonia composition the hair coloring method comprises mixing a coloring composition a) of the kit as defined above with an alkalizing composition b) of the kit as defined above, as follows:

for shades from 1 to 6, adding the composition b) to the composition a) in such an amount as to obtain from 0.5% to 1.2%, preferably 0.8%, of alkalizing agent, in order to obtain a medium basic pH coloring; or adding the composition b) to the composition a) in such an amount as to obtain from 1.2% to 2.8%, preferably 1.6%, of alkalizing agent, in order to obtain a basic pH coloring;

for shade from 7 to 10, adding the composition b) to the composition a) in such an amount as to obtain from 0.7% to 1.8%, preferably 1%, of alkalizing agent, in order to obtain a medium basic pH coloring; or adding the composition b) to the composition a) in such an amount as to obtain from 1.8% to 3.5%, preferably 2%, of alkalizing agent, in order to obtain a basic pH coloring;

for super-lighteners (shade 12), adding the composition b) to the composition a) in such an amount as to obtain from 0.7% to 1.2%, preferably 1%, of alkalizing agent, in order to obtain a medium basic pH coloring; or adding the composition b) to the composition a) in such an amount as to obtain from 1.2% to 5%, preferably 3%, of alkalizing agent, in order to obtain a basic pH coloring; said percentages being by weight with respect to the sum of the weight of the coloring composition and of the weight of the composition comprising the alkalizing agent.

Medium basic pH means a pH value no greater than 8.5.

The composition obtained can then be applied on hair.

According to the knowledge of the person skilled in the art, when an alkalizing agent other than ammonia is used, the above-mentioned percentages can be varied based on the strength of the alkalizing agent itself.

The alkalizing composition b), also called booster, can comprise ammonia in the form of ammonium hydroxide as described above and in the examples. According to the present invention, two types of BOOSTERS can be used, one for shades 1-6 and one for shades 7-10 and 12.

The present invention also relates to an acidic pH hair coloring method comprising the use of a coloring composition as defined above to obtain shades 1 to 6, shades 7 to 10 or super-lighteners (shade 12).

The method according to the present invention can further comprise adding an oxidizing composition c) of the kit as defined above, for example in a ratio of coloring composition to oxidizing composition from 1:1 to 1:4, for example 1:1, 1:1.5, 1:2, 1:3 or 1:4.

The composition obtained is then applied on hair.

DESCRIPTION OF SPECIFIC EMBODIMENTS OF THE INVENTION

The invention will be described below by way of illustration and not by way of limitation, with particular reference to some illustrative examples.

Example 1

Base Coloring Cream Formulations

The cases include all formulations in the category of emulsions, wherein, therefore, a fat phase and an aqueous phase are present.

The percentages of the ingredients are by weight with respect to the weight of the coloring formulation. The ingredients are listed in subgroups called phases for the sake of simplicity in the description of the method for preparing the formulation.

Phase 1
CETYLSTEARYL ALCOHOL 15% (or other alcohols and fatty acids, similarly of natural derivation)
OLIVE OIL 3% (or other vegetable oils)
JOJOBA WAX 5% (or other plant waxes such as mimosa wax, rice wax, etc., or animal waxes, if the product not is vegan, such as beeswax, lanolin wax, etc.)
SHEA BUTTER 5% (or other natural butters)
CAPRYLIC-CAPRIC TRIGLYCERIDE 3% (or other emollient oils of natural derivation)
Phase 2
PROPANEDIOL 10% (or other solvents of plant origin)
LAURYL GLUCOSIDE 5% (or other surfactants of plant origin)
ASCORBIC ACID 0.5% (or other antioxidant agents of natural origin)
NATURAL CHELATING AGENT 2%
SODIUM BISULFITE 0.2%
ALKALIZING AGENT (a small percentage is added, which serves to bind the dyes and solubilize them in the form of salts, thus making them available within the formulation; the percentage of alkalizing agent is calculated stoichiometrically on the basis of the exact moles of dye introduced into the specific shade. This addition is defined technical because the alkalizing agent, once the formulation is completed, will not be present in a free form, but only in a form bound to the dyes, and it thus does not participate in the pH of the formulation; in any case, however, it is indicated in INCI labels).
WATER (q.s. to 100%)
Phase 3
DYES (in different percentages according to the selected shade)
Phase 4
a.i. (various active ingredients) 3%
Method of Preparation:
Phases 1 and 2 are brought to a temperature of about 80° C. The dyes of the phase 3 are dissolved in phase 2. The two phases are mixed together, under appropriate stirring, until a homogeneous emulsion is obtained. At this point, the temperature is gradually decreased and the final phase of the active ingredients is added.

All the substances selected on the basis of the specific features it is desired to give to the formulation are included in the category of active ingredients, for example functional active ingredients that have protective properties when it is desired to impart a hair protective function to the formulation.

Example 2

Base Coloring Gel Formulations

The cases include all formulations that provide for the use of a gelling agent.

Phase 1
PROPANEDIOL 10% (or other solvents of plant origin)
LAURYL GLUCOSIDE 5% (or other surfactants of plant origin)
ASCORBIC ACID 0.5% (or other antioxidant agents of natural origin)
NATURAL CHELATING AGENT 2%
SODIUM BISULFITE 0.2%
ALKALIZING AGENT (a small percentage is added, which serves to bind the dyes and solubilize them in the form of salts, thus making them available within the formulation; the percentage of alkalizing agent is calculated stoichiometrically on the basis of the exact moles of dye introduced into the specific shade. This addition is defined technical because the alkalizing agent, once the formulation is completed, will not be present in a free form, but only in a form bound to the dyes, and it thus does not participate in the pH of the formulation; in any case, however, it is indicated in INCI labels).
WATER (q.s. to 100%)
Phase 2
DYES (in different percentages according to the selected shade)
Phase 3
a.i. (various active ingredients) 3%
Phase 4
NATURAL GELLING AGENT 1%
PROPANEDIOL 10% (or other solvents of plant origin)
Method of Preparation:

Phase 1 is brought to a temperature of 60° C. or higher (depending on the dyes selected). PHASE 2 of the dyes is added to this and they are brought to complete dissolution.

Once a homogeneous solution has been obtained, phase 3 of the active ingredients is added, the mixture is homogenized and phase 4 of the viscosifying agent is added.

Example 3

Booster Formulation

The cases include all formulations in the category of emulsions, wherein, therefore, a fat phase and an aqueous phase are present, and wherein the alkalizing agent is present in the amounts necessary to perform its BOOSTER action.

The percentages of the ingredients are by weight with respect to weight of the alkalizing formulation. The ingredients are listed in subgroups called phases for the sake of simplicity in the description of the method for preparing the formulation.

Phase 1
CETYLSTEARYL ALCOHOL 25% (or other alcohols and fatty acids, similarly of natural derivation)
OLIVE OIL 2% (or other vegetable oils)
JOJOBA WAX 2% (or other plant waxes such as mimosa wax, rice wax, etc., or animal waxes, if the product not is vegan, such as beeswax, lanolin wax, etc.)
SHEA BUTTER 2% (or other natural butters)
CAPRYLIC-CAPRIC TRIGLYCERIDE 2% (or other emollient oils of natural derivation)
Phase 2
PROPANEDIOL 10% (or other solvents of plant origin)
NATURAL CHELATING AGENT 2%
Phase 3
ALKALIZING AGENT (NH4OH) 27% in BOOSTER 01 33% in BOOSTER 02
WATER (q.s. to 100%)
Phase 4
a.i. (various active ingredients) 3%
Method of Preparation Phases 1 and 2 are brought to a temperature of about 80° C. The two phases are mixed together, under appropriate stirring, until a homogeneous emulsion is obtained. At this point, the temperature is gradually decreased and phase 3 is added, again gradually, along with the final phase 4 of the active ingredients.

Example 4

Formulation Containing Oxidizing Agent

The cases include all formulations in the category of emulsions, wherein, therefore, a fat phase and an aqueous phase are present, and wherein the oxidizing agent is present in the amounts necessary to perform its specific action.

The percentages of the ingredients are by weight with respect to weight of the oxidizing formulation. The ingredients are listed in subgroups called phases for the sake of simplicity in the description of the method for preparing the formulation.

Phase 1
CETYLSTEARYL ALCOHOL 25% (or other alcohols and fatty acids, similarly of natural derivation)
OLIVE OIL 2% (or other vegetable oils)
JOJOBA WAX 2% (or other plant waxes such as mimosa wax, rice wax, etc., or animal waxes, if the product not is vegan, such as beeswax, lanolin wax, etc.)
SHEA BUTTER 2% (or other natural butters)
CAPRYLIC-CAPRIC TRIGLYCERIDE 2% (or other emollient oils of natural derivation)
Phase 2
PROPANEDIOL 10% (or other solvents of plant origin)
PHOSPHORIC ACID 0.5% max
ETIDRONIC ACID 0.5% max
or other acidifying and/or stabilizing agents of the oxidizing formulation
Phase 3
$H_2O_2$ (130 vol hydrogen peroxide solution introduced in different percentages according to the volume of oxygen it is desired to achieve)
WATER (q.s. to 100%)
Phase 4
ACRYLATES AND METHACRYLATES 5% (or natural derivatives such as those of cellulose)
Method of Preparation Phases 1 and 2 are brought to a temperature of about 80° C. The two phases are mixed together, under appropriate stirring, until a homogeneous emulsion is obtained. At this point, the temperature is gradually decreased and phase 3 is added, again gradually, along with the final phase 4 of the viscosifiers.

Example 5

Coloring Test

For every type of formulation produced, the following test protocol was adopted:

Product Functional Tests

STRAND TEST: for all types of colorings, the following strands were used:

NATURAL BROWN SHADE 5 (to simulate the result on untreated brown hair);

SALT&PEPPER (natural hair shade 5 with 50% of natural white hair; to simulate the effect of white hair coverage);

DECOLORED (strand decolorized to shade 8-9 to simulate the effect of coloring on treated, sensitized hair);

YAK (completely white goat hair, which serves to visualize the pure reflection of the color).

In addition to strands of hair, use is also made of a MULTIFIBRE DW 2 fabric (by Ausiliari Tessili), which serves to visualize the reflection and the color level on different types of natural fiber (cotton, wool, nylon etc.). This approach is used because the color absorption of some textile fibers is very similar to that of hair fibers.

The results obtained are then read by means of a KONIKA MINOLTA CM30d SPECTROPHOTOMETER, which expresses the results in values of L (luminous intensity) and ab (reflections).

In 1976, the CIE developed the L*a*b calorimetric model (also known by the name of CIELAB), wherein a color is identified by three values:

L, luminance, expressed as a percentage (0 for black and 100 for white);

a and b, two ranges of colors respectively from green to red and from blue to yellow, with values from −120 to +120.

The Lab method thus covers the entire spectrum visible to the human eye and represents it in a uniform manner. It thus enables the set of visible colors to be described independently of any graphic technology.

TESTS ON THE HEAD: once the tests on strands and fabric have received approval, one proceeds to tests on the head. In this case there is greater information, given by the difference in hair structure, whether the hair is more or less natural or treated, and whether the scalp is more or less sensitive.

RESULTS: for every test conducted we obtained satisfactory results from the viewpoint both of the reflection and of the hair color level (compared with known market benchmarks), from the viewpoint of color fastness to washing and exposure to sunlight, and from the viewpoint of the compliance of the model who underwent the tests, who never complained of skin discomfort and showed complete satisfaction with the color result and fastness. Overall, we performed about 1,000 strand tests and about 500 tests on model.

Product Stability Test

Simultaneously with the functionality tests, product stability tests are performed by storing the various formulations in an oven at 40° C. and stressing them with storage in an oven at 40° C. alternated with storage in a freezer at about −5° C.-10° C.

PRODUCT TOXICITY TESTS: before tests were performed on the head, dermatological tests were conducted by external institutes (e.g. ISPE and MEURIEUX), to assay, by means of patch tests on healthy volunteers, both the potential skin irritation and the allergizing potential. It emerged from these tests that the product, in all its versions and forms, has a skin irritation potential, both immediate and delayed (in 48 h), equal to 0, therefore, a high skin tolerance.

Example 5

Mixing of the Components of the Kit According to the Present Invention Based on the Desired Shades The percentages of booster to be added to the coloring composition, wherein the booster 01 contains 27% $NH_4OH$ and the booster 02 contains 33% NH4OH, are specified below.

Shades from 1 to 6
ACHIEVABLE COLORINGS:
acidic pH: 0% BOOSTER 01
medium-basic pH: 10% BOOSTER 01
basic pH: 20% BOOSTER 01
Shades from 7 to 10
ACHIEVABLE COLORINGS:
acidic pH: 0% BOOSTER 02
medium-basic pH: 10% BOOSTER 02
basic pH: 20% BOOSTER 02
Shade 12
ACHIEVABLE COLORINGS:
acidic pH: 0% BOOSTER 02
medium-basic pH: 10% BOOSTER 02
basic pH: 30% BOOSTER 02

The application is completed by the addition of the third component, i.e. the one containing the oxidizing agent, HYDROGEN PEROXIDE. Descriptive examples follow:

Shades from 1 to 6
ACHIEVABLE COLORINGS:
acidic pH: 0% BOOSTER 01
selected shade (50 g)+oxidizing component c) (50 g)
medium-basic pH: 10% BOOSTER 01
selected shade (50 g)+oxidizing component c) (50 g)+component b) BOOSTER 01 (5 g)
basic pH: 20% BOOSTER 01
selected shade (50 g)+oxidizing component c) (50 g)+component b) BOOSTER 01 (10 g)
Shades from 7 to 10
ACHIEVABLE COLORINGS:
acidic pH: 0% BOOSTER 02
selected shade (50 g)+oxidizing component c) (50 g)
medium-basic pH: 10% BOOSTER 02
selected shade (50 g)+oxidizing component c) (50 g)+component b) BOOSTER 02 (5 g)
basic pH: 20% BOOSTER 02
selected shade (50 g)+oxidizing component c) (50 g)+component b) BOOSTER 02 (10 g)
Shade 12
ACHIEVABLE COLORINGS:
acidic pH: 0% BOOSTER 02
selected shade (50 g)+oxidizing component c) (50 g)
medium-basic pH: 10% BOOSTER 02
selected shade (50 g)+oxidizing component c) (50 g)+component b) BOOSTER 02 (5 g)
basic pH: 30% BOOSTER 02
selected shade (50 g)+oxidizing component c) (100 g)+component b) BOOSTER 02 (15 g)

The present invention has been described for non-limiting illustrative purposes, according to its preferred embodiments, but it is to be considered that any variations and/or modifications may be made by persons skilled in the art without departing from the relative scope of protection, as defined by the appended claims.

What is claimed is:

1. A hair coloring kit comprising:
a) a coloring composition,
b) an alkalizing composition comprising one or more alkalizing agents, and
c) an oxidizing composition that comprises one or more oxidizing agents,
wherein said coloring composition is in the form of a gel that comprises:
one or more natural solvents in a percentage ranging from 0.1% to 90%;
one or more natural surfactants in a percentage ranging from 0.1% to 30%;
gums as viscosifiers, wherein said viscosifiers are in a percentage ranging from 0.01% to 10%; said percentages being by weight with respect to the coloring composition; and
dyes or their oxidation intermediates.

2. A hair coloring method comprising mixing a coloring composition a) with an alkalizing composition b), wherein:
a) the coloring composition comprises:
one or more natural solvents in a percentage ranging from 0.1% to 90%;
one or more natural surfactants in a percentage ranging from 0.1% to 30%;
viscosifiers or consistency factors, wherein said viscosifiers are in a percentage ranging from 0.01% to 10%, while said consistency factors are in a percentage ranging from 1% to 50%; said percentages being by weight with respect to the coloring composition, and
dyes or their oxidation intermediates, and
b) an alkalizing composition comprises ammonia as alkalizing agent,
wherein
said mixing is effected as follows:
for shades from 1 to 6, adding the composition b) to the composition a) in such an amount as to obtain from 0.5% to 1.2% of ammonia, in order to obtain a medium basic pH coloring; or adding the composition b) to the composition a) in such an amount as to obtain from 1.2% to 2.8% of ammonia, in order to obtain a basic pH coloring;
for shades from 7 to 10, adding the composition b) to the composition a) in such an amount as to obtain from 0.7% to 1.8% of ammonia, in order to obtain a medium basic pH coloring; or adding the composition b) to the composition a) in such an amount as to obtain from 1.8% to 3.5% of ammonia, in order to obtain a basic pH coloring;
for super-lighteners (shade 12), adding the composition b) to the composition a) in such an amount as to obtain from 0.7% to 1.2% of ammonia, in order to obtain a medium basic pH coloring; or adding the composition b) to the composition a) in such an amount as to obtain from 1.2% to 5% of ammonia, in order to obtain a basic pH coloring; said percentages being by weight with respect to the sum of the weight of the coloring composition and of the weight of the alkalizing composition.

3. A hair coloring method comprising applying on hair a coloring composition with an acidic pH to obtain the shades from 1 to 6, shades from 7 to 10 or super-lighteners (shade 12), wherein said coloring composition is in the form of a gel that comprises:
one or more natural solvents in a percentage ranging from 0.1% to 90%;
one or more natural surfactants in a percentage ranging from 0.1% to 30%;
gums as viscosifiers, wherein said viscosifiers are in a percentage ranging from 0.01% to 10%; said percentages being by weight with respect to the coloring composition; and
dyes or their oxidation intermediates.

4. A hair coloring method comprising mixing a coloring composition a) with an alkalizing composition b), and adding an oxidizing composition c) comprising one or more oxidizing agents, wherein:
a) said coloring composition comprises:
one or more natural solvents in a percentage ranging from 0.1% to 90%;
one or more natural surfactants in a percentage ranging from 0.1% to 30%;
viscosifiers or consistency factors, wherein said viscosifiers are in a percentage ranging from 0.01% to 10%, while said consistency factors are in a percentage ranging from 1% to 50%; said percentages being by weight with respect to the coloring composition, and
dyes or their oxidation intermediates, and
b) the alkalizing composition comprises one or more alkalizing agents;
wherein the composition b) is added to the composition a) in such an amount as to obtain from 0.5 to 10% of alkalizing agent.

5. The kit of claim 1, wherein the oxidizing composition comprises:
one or more natural solvents in a percentage ranging from 0.1% to 90%;
one or more natural surfactants in a percentage ranging from 0.1% to 30%;
viscosifiers or consistency factors, wherein said viscosifiers are in a percentage ranging from 0.01% to 10%; said percentages being by weight with respect to the oxidizing composition,
one or more oxidizing agents.

6. The kit of claim 1, wherein said alkalizing composition comprises:
one or more natural solvents in a percentage ranging from 0.1% to 90%;
one or more natural surfactants in a percentage ranging from 0.1% to 30%;
viscosifiers or consistency factors, wherein said viscosifiers are in a percentage ranging from 0.01% to 10%; said percentages being by weight with respect to the alkalizing composition; and
one or more alkalizing agents.

7. The kit of claim 1, wherein said oxidizing composition is in a form of cream and comprises:
one or more natural solvents in a percentage ranging from 0.1% to 90%;
one or more natural surfactants in a percentage ranging from 0.1% to 30%;
viscosifiers and/or consistency factors, wherein said viscosifiers are in a percentage ranging from 0.01% to 10%; said percentages being by weight with respect to the oxidizing composition; and
one or more oxidizing agents.

8. The method of claim 4, wherein said oxidizing composition is in a form of cream and comprises:
one or more natural solvents in a percentage ranging from 0.1% to 90%;
one or more natural surfactants in a percentage ranging from 0.1% to 30%;
viscosifiers or consistency factors, wherein said viscosifiers are in a percentage ranging from 0.01% to 10%, while said consistency factors are in a percentage ranging from 1% to 50%; said percentages being by weight with respect to the oxidizing composition; and
one or more oxidizing agents.

9. The kit of claim 1, wherein said one or more alkalizing agents are ammines selected from ammonia, monoethanolamine, aminomethyl propanol, arginine or other amino acids or tris (tris(hydroxymethyl)aminomethane).

10. The method according to claim 2, wherein the alkalizing composition comprises
one or more natural solvents in a percentage ranging from 0.1% to 90%;
one or more natural surfactants in a percentage ranging from 0.1% to 30%;
viscosifiers or consistency factors, wherein said viscosifiers are in a percentage ranging from 0.01% to 10%, while said consistency factors are in a percentage ranging from 1% to 50%; said percentages being by weight with respect to the alkalizing composition, and
ammonia.

11. The method according to claim 2, wherein the viscosifiers are selected from xanthan gum, *Sclerotium* gum, guar gum, gum arabic, gum derived from sugars and wherein the consistency factors are selected from waxes, fatty alcohols and/or fatty acids.

12. The method according to claim 4, wherein the alkalizing composition comprises
one or more natural solvents in a percentage ranging from 0.1% to 90%;
one or more natural surfactants in a percentage ranging from 0.1% to 30%;
viscosifiers or consistency factors, wherein said viscosifiers are in a percentage ranging from 0.01% to 10%, while said consistency factors are in a percentage ranging from 1% to 50%; said percentages being by weight with respect to the alkalizing composition, and
one or more alkalizing agents to obtain an alkalizing composition.

13. The method according to claim 4, wherein said one or more alkalizing agents are ammines selected from ammonia, monoethanolamine, aminomethyl propanol, arginine or other amino acids or tris (tris(hydroxymethyl)aminomethane).

14. The method according to claim 4, wherein the viscosifiers are selected from xanthan gum, *Sclerotium* gum, guar gum, gum arabic, gum derived from sugars and wherein the consistency factors are selected from waxes, fatty alcohols and/or fatty acids.

* * * * *